United States Patent
Kosi-Kupe

(10) Patent No.: US 10,195,171 B2
(45) Date of Patent: Feb. 5, 2019

(54) PROCESS OF PREPARATION OF NUTRITIONAL SUPPLEMENT CONTAINING SULFORAPHANE

(71) Applicant: Anne-Marie Kosi-Kupe, Greenwood, IN (US)

(72) Inventor: Anne-Marie Kosi-Kupe, Greenwood, IN (US)

(73) Assignee: CLOJJIC LLC, Greenwood, IN (US)

(*) Notice: Subject to any disclaimer, the term of this patent is extended or adjusted under 35 U.S.C. 154(b) by 0 days.

(21) Appl. No.: 15/081,713

(22) Filed: Mar. 25, 2016

(65) Prior Publication Data

US 2016/0279090 A1    Sep. 29, 2016

Related U.S. Application Data

(60) Provisional application No. 62/138,035, filed on Mar. 25, 2015.

(51) Int. Cl.
| | |
|---|---|
| *A61K 31/26* | (2006.01) |
| *A61K 35/745* | (2015.01) |
| *A61K 35/747* | (2015.01) |
| *A61K 36/31* | (2006.01) |
| *A23L 19/00* | (2016.01) |
| *A23L 33/105* | (2016.01) |
| *A23L 33/135* | (2016.01) |

(52) U.S. Cl.
CPC .............. *A61K 31/26* (2013.01); *A23L 19/00* (2016.08); *A23L 33/105* (2016.08); *A23L 33/135* (2016.08); *A61K 35/745* (2013.01); *A61K 35/747* (2013.01); *A61K 36/31* (2013.01); *A23V 2002/00* (2013.01); *A23Y 2220/03* (2013.01); *A23Y 2220/13* (2013.01); *A23Y 2220/15* (2013.01); *A23Y 2220/63* (2013.01); *A23Y 2220/67* (2013.01); *A23Y 2220/73* (2013.01); *A23Y 2220/79* (2013.01); *A23Y 2240/75* (2013.01); *A23Y 2300/25* (2013.01); *A23Y 2300/45* (2013.01); *A23Y 2300/49* (2013.01); *A23Y 2300/55* (2013.01); *A61K 2236/19* (2013.01)

(58) Field of Classification Search
CPC .............. A61K 2300/00; A61K 31/122; A61K 31/593; A61K 33/00; A61K 33/06; A61K 33/26; A61K 33/30; A61K 33/32; A61K 33/34; A61K 33/42; A61K 36/31; A61K 35/747; A61K 35/745; A61K 36/48; A61K 45/06; A61K 31/047; A61K 31/19; A61K 31/716; A61K 31/202; A61K 31/59; A61K 38/40; A61K 31/26; A61K 2035/11; A61K 2236/19; A61K 31/688; A61K 31/70; A61K 35/20; A61K 35/741; A61K 35/744; A61K 38/018; A23V 2002/00; A23V 2200/30; A23V 2200/3262; A23V 2250/21; A23V 2250/641; A23V 2200/00; A23V 2200/3202; A23V 2200/322; A23V 2250/00; A23V 2250/1882; A23V 2250/1884; A23V 2250/1946; A23V 2250/5034; A23V 2220/03; A23Y 2220/73; A23Y 2220/03; A23Y 2220/13; A23Y 2220/15; A23Y 2220/63; A23Y 2220/67; A23Y 2220/79; A23Y 2240/75; A23Y 2300/25; A23Y 2300/45; A23Y 2300/49; A23Y 2300/55; A23L 33/135; A23L 33/10; A23L 33/105; A23L 33/12; A23L 33/40; A23L 33/17; A23L 33/18; A23L 19/00; A23L 1/212; A23L 1/3014; A23L 33/115; A23L 33/125; A23L 33/15; A23L 33/155; A23L 33/16; A23L 33/19; A23L 33/21; A23L 33/30; A23L 1/296; G06F 19/3475; Y02A 90/26; A61P 3/00; A61P 3/02; A61P 3/04; A61P 3/08
See application file for complete search history.

(56) References Cited

U.S. PATENT DOCUMENTS

| | | | |
|---|---|---|---|
| 8,124,135 B2 | 2/2012 | Pietrzkowski | |
| 2009/0098225 A1* | 4/2009 | Pietrzkowski | ......... A61K 36/31 424/755 |
| 2011/0091587 A1 | 4/2011 | Blackwell et al. | |
| 2011/0206721 A1 | 8/2011 | Nair | |
| 2014/0271978 A1 | 9/2014 | Wittke et al. | |

FOREIGN PATENT DOCUMENTS

WO    2013015666    1/2013

* cited by examiner

*Primary Examiner* — Deborah K Ware
(74) *Attorney, Agent, or Firm* — Hartman Global IP Law; Gary M. Hartman; Domenica N. S. Hartman

(57) ABSTRACT

Processes for producing a nutritional supplement that contains sulforaphane, and supplements formed thereby. Such a process includes combining a cruciferous vegetable, for example, broccoli sprouts, with strains of *Lactobacillus, Streptococcus* and *Bifidobacterium* to form a mixture, causing the mixture to undergo lactic acid fermentation, transform a glucosinolate within the cruciferous vegetable to sulforaphane, and yield a fermented mixture that contains sulforaphane, and then producing from the fermented mixture a supplement that can be ingested by an individual.

10 Claims, 1 Drawing Sheet

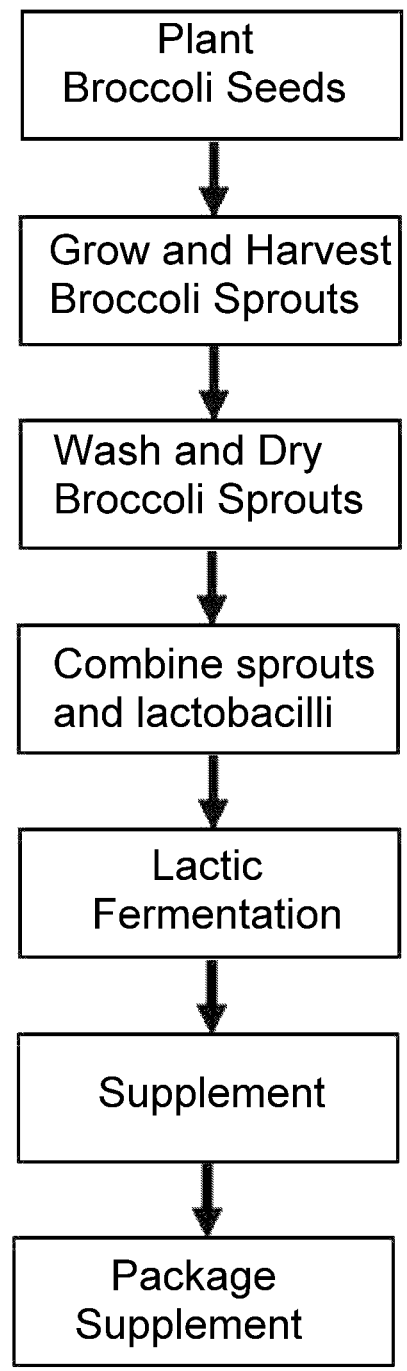

PROCESS OF PREPARATION OF NUTRITIONAL SUPPLEMENT CONTAINING SULFORAPHANE

CROSS REFERENCE TO RELATED APPLICATIONS

This application claims the benefit of U.S. Provisional Application No. 62/138,035, filed Mar. 25, 2015, the contents of which are incorporated herein by reference.

BACKGROUND OF THE INVENTION

The present invention generally relates to dietary and nutritional supplements, and particularly to processes for producing a nutritional supplement that contains sulforaphane.

Sulforaphane is known as a long-lasting antioxidant whose anti-cancerogenic effects were confirmed by in-vitro studies conducted by John Hopkins University School of Medicine in 1992. Sulforaphane is obtained from cruciferous vegetables (the family Brassicaceae, also called Cruciferae), nonlimiting examples of which include Brussels sprouts, cabbages, cauliflower, broccoli (particularly broccoli sprouts), and similar green leaf vegetables. More particularly, cruciferous vegetables contain glucoraphanin (a glucosinolate), which reacts with myrosinase (an enzyme present in the plant cell) to form sulforaphane. The reaction between myrosinase and glucosinolate occurs in the gut after glucosinolate is made available by chewing, such that sulforaphane is produced after eating.

Despite their nutritional and health benefits, including being a source of sulforaphane, broccoli sprouts have certain disadvantages that have limited their use. For example, broccoli sprouts tend to spoil quickly and contamination with coliform bacteria is a known safety issue, with the result that the consumption of broccoli sprouts is often accompanied by unwanted additives. A variety of sulforaphane powders, pills and probiotics are commercially available. However, sulforaphane powder mixed in water is only stable over a short period and must be consumed as soon as possible, often within thirty minutes of mixing.

Accordingly, there is a desire for a convenient and durable source of sulforaphane that is capable of delivering the nutritional benefits of sulforaphane, aside from the direct consumption of fresh broccoli sprouts.

BRIEF DESCRIPTION OF THE INVENTION

The present invention provides a process for producing a nutritional supplement that contains sulforaphane, and supplements formed thereby.

According to one aspect of the invention, a process of producing a sulforaphane-containing nutritional supplement includes combining a cruciferous vegetable, for example, broccoli sprouts, with at least one strain of *Lactobacillus* to form a mixture, causing the mixture to undergo lactic acid fermentation, transform a glucosinolate within the cruciferous vegetable to sulforaphane, and yield a fermented mixture that contains sulforaphane, and then producing from the fermented mixture a supplement that can be ingested by an individual.

Another aspect of the invention is a supplement produced by a process comprising the steps described above.

Technical effects of the process and supplement as described above preferably include the ability to provide a source of sulforaphane that is capable of delivering the nutritional benefits of sulforaphane, but avoids drawbacks associated with the consumption of cruciferous vegetables such as broccoli sprouts.

Other aspects and advantages of this invention will be further appreciated from the following description.

BRIEF DESCRIPTION OF THE DRAWINGS

FIG. 1 represents a flow diagram of a process for producing a nutritional supplement in accordance with a non-limiting embodiment of this invention.

DETAILED DESCRIPTION OF THE INVENTION

An overview of a process for producing a sulforaphane-containing nutritional supplement is represented in FIG. 1. The process is microbiologically safe and yields a durable natural formula that contains sulforaphane prior to being ingested by an individual, and is capable of delivering benefits to the individual when ingested.

FIG. 1 and the following discussion will make specific reference to the production of sulforaphane from broccoli sprouts, though it is foreseeable that the steps disclosed below are applicable to the production of sulforaphane from other cruciferous vegetables (Brassicaceae). As outlined in FIG. 1, broccoli seeds are preferably sanitized before being planted to grow broccoli sprouts. As used herein, the term broccoli sprouts will refer to new growth from seed germination, for example, a plant that is a few (e.g., three to four) days old. After harvest, the sprouts are preferably washed and dried, for example, to reduce the presence of bacteria on the sprouts. The sprouts are then combined with ingredients that, in investigations leading to the present invention, were shown to trigger a lactic acid fermentation that transforms glucosinolate contained in the sprouts to sulforaphane. Fermentation produces sulforaphane without requiring chewing or otherwise physically breaking up the sprouts to make the glucosinolate available and without the requirement for contacting and reacting the sprouts with myrosinase. According to a particular but nonlimiting embodiment of the invention, the broccoli sprouts are combined with multiple strains of *Lactobacillus*, which are part of the lactic acid bacteria (LAB) group and known as probiotics. In combination, lactobacilli strains employed by the process have been found to trigger a lactic acid fermentation that transforms glucosinolate to sulforaphane, yielding a sulforaphane-containing product ("supplement").

The fermentation has been successfully conducted in anaerobic and dark environments (i.e., shielded from and preferably in the absence of natural and artificial lighting) at room temperatures (for example, about 20° C.). The fermentation step has been successfully conducted in manmade containers, and is believed will occur within a wide variety of container. As such, the process results in the presence of sulforaphane in the supplement, instead of sulforaphane becoming available in the human gut (gastrointestinal tract) after consumption of the supplement. The supplement can be considered to be a sulforaphane-probiotics hybrid product having notable nutritional benefits, derived in part from vitamins and minerals that are naturally present in the supplement as a result of being present in the broccoli sprouts from which the supplement was produced.

The reaction that forms the sulforaphane does not require that the sulforaphane-containing supplement is produced in the form of a pill or powder. Instead, the supplement produced by the fermentation process can remain in the form of a consumer food item, in other words, a food item that can be directly ingested by an individual instead of being further processed, for example, to extract the sulforaphane for consumption as a concentrated supplement. Such a food item can be essentially fermented broccoli sprouts that can be packaged for consumption as a salad, as an ingredient to a salad, sandwich, soup, etc., as a condiment, or added to a processed food product such as a snack, yogurt, drink, etc.

In view of the above, though referred to as a supplement, the fermented broccoli sprouts can be made available as food items in a variety of physical forms. In addition to consumer food items, the supplement may be processed and packaged for use by medical personnel, nutritionalists, etc., in a variety of industries and practices, for example, as a pill, powder, etc., for use in pharmaceuticals, nutraceuticals, preventative medicines, food processors, etc. In each case, the ultimate intent is for the supplement to be consumed by an individual, namely, ingested through the mouth and into the gastrointestinal tract. The supplement can be particularly beneficial to individuals with digestive or other health issues. The shelf-life of the supplement is believed to be several months at temperatures over a range of about 10 to about 15° C.

In a particular investigation, organic broccoli sprouts germinated over three days were washed three times in non-chlorinated purified water, after which the following twelve selected strains of lactobacilli were added: *B. bifidum, B. lactis, B. infantis, B. longum, L. acidophilus, L. brevis, L. bulgaricus, L. paracasei, L. plantarum, L. rhamnosus, L. salivaricus*, and *Streptococcus thermophilus*. These strains were chosen on the basis of having known physiological benefits and antimicrobial capabilities. Sea salt was added to this mixture to create an acidic pH suitable for lactic acid fermentation, which was conducted in an anaerobic and dark environment at about 20° C. After three days at these conditions, the mixture was found to be fermented and the mixture tested positive (0.130 mg/g) for sulforaphane. The LAB content of the mixture remained high (31000 cells/g) and no coliform bacteria was detected. Coliform bacteria was not detected following storage of the fermented mixture in a refrigerator over a two-month period.

While the invention has been described in terms of certain embodiments, it is apparent that other forms could be adopted by one skilled in the art. For example, though twelve specific strains of *Lactobacillus* were used in the investigation, it may be possible that certain of the used strains could be omitted or other *lactobacilli* could be used and yet yield a fermentation that will produce a suitable fermented mixture that contains sulforaphane. In addition, it is foreseeable that multiple cruciferous vegetable could be combined and fermented. Accordingly, it should be understood that the invention is not limited to any embodiment described herein. It should also be understood that the phraseology and terminology employed above are for the purpose of describing the disclosed embodiments, and do not necessarily serve as limitations to the scope of the invention. Therefore, the scope of the invention is to be limited only by the following claims.

The invention claimed is:

1. A process for producing a sulforaphane-containing nutritional supplement, the process comprising:
   combining a cruciferous vegetable with strains of *Lactobacillus, Streptococcus* and *Bifidobacterium* to form a mixture, wherein the strains of *Lactobacillus, Streptococcus* and *Bifidobacterium* comprise each of *B. bifidum, B. lactis, B. infantis, B. longum, L. acidophilus, L. brevis, L. bulgaricus, L. paracasei, L. plantarum, L. rhamnosus, L. salivaricus*, and *Streptococcus thermophilus*;
   causing the mixture to undergo lactic acid fermentation in a container, transform a glucosinolate within the cruciferous vegetable to sulforaphane, and yield a fermented mixture that contains sulforaphane; and
   producing from the fermented mixture a supplement that can be orally ingested by an individual into the gastrointestinal tract, wherein the fermented mixture has an undetectable amount of coliform bacteria after at least two months refrigerator storage and has a shelf life of more than two months at a temperature of about 10 degrees to about 15 degrees Celsius.

2. The process according to claim 1, wherein the cruciferous vegetable is broccoli sprouts.

3. The process according to claim 2, further comprising adding at least a second cruciferous vegetable other than broccoli sprouts to the mixture prior to the lactic acid fermentation thereof.

4. The process according to claim 1, wherein the mixture has an acidic pH during the lactic acid fermentation of the mixture.

5. The process according to claim 4, wherein the acidic pH is obtained by adding salt to the mixture.

6. The process according to claim 1, wherein the lactic acid fermentation is conducted in an anaerobic and dark environment at about 20° C.

7. The process according to claim 1, wherein the supplement is a consumer food item.

8. The process according to claim 7, wherein the consumer food item is fermented broccoli sprouts.

9. The process according to claim 1, wherein the supplement is a pill or powder.

10. The process according to claim 1, wherein the supplement is a sulforaphane-probiotics hybrid product that further contains the strains of *Lactobacillus, Streptococcus* and *Bifidobacterium*.

\* \* \* \* \*